United States Patent
Spangler et al.

(10) Patent No.: US 6,524,574 B1
(45) Date of Patent: Feb. 25, 2003

(54) PROBIOTIC MIXTURE INTENDED FOR MONOGASTRIC ANIMALS TO CONTROL INTESTINAL FLORA POPULATIONS

(75) Inventors: David A. Spangler, Fulton, IL (US); Patrick K. Brown, Fulton, IL (US); Thomas E. Witzig, Rochester, MN (US)

(73) Assignees: Agri-King, Inc., Fulton, IL (US); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/087,792

(22) Filed: May 29, 1998

(51) Int. Cl.$^7$ ................................. A01N 63/00
(52) U.S. Cl. ................ 424/93.3; 424/93.45; 424/93.51; 424/93.48
(58) Field of Search ...................... 435/252.4; 424/93.3, 424/93.48, 93.45, 93.51

(56) References Cited

U.S. PATENT DOCUMENTS

| | | | | |
|---|---|---|---|---|
| 4,192,918 A | * | 3/1980 | Stineman et al. | 435/256 |
| 5,185,165 A | * | 2/1993 | Lynn | 426/61 |
| 5,340,577 A | * | 8/1994 | Nisbet et al. | 424/93.21 |
| 5,968,569 A | * | 10/1999 | Cavadini et al. | 426/61 |
| 5,976,580 A | * | 11/1999 | Ivey et al. | 426/2 |
| 6,221,350 B1 | | 4/2001 | Brown et al. | 424/93.3 |

FOREIGN PATENT DOCUMENTS

PH 29583 A * 4/1996

OTHER PUBLICATIONS

Collar et al. Z. Lebesm. Unters. Forsch. (1991), 193:332–336.*
Canganella et al. Microbiol. res. (1997), 152: 171–179.*
Adlerberth et al. Applied and Environmental Microbiology. 1996. vol. 62, No. 7, pp. 2244–2251.*
Webster's Dictinary. 1988. pp. 78–79, 1158.*
Elmer et al. JAMA . Mar. 1996. vol. 275, No. 11, pp. 870–876.*
Hamilton–Miller J.M.T. Clinical Microbiology and Infection. 1997. 3/1, pp. 2–4.*

* cited by examiner

*Primary Examiner*—Irene Marx
*Assistant Examiner*—Vera Afremova
(74) *Attorney, Agent, or Firm*—Brian J. Laurenzo; W. Robinson; H. Clark (57) ABSTRACT

A mixture of probiotics effective to reduce the contamination of enteric bacteria in humans and other monogastric animals. The mixture of probiotics includes a lactic acid-producing bacteria and a yeast, and may advantageously be supplemented with a source of nutrients, such as lactose, in certain applications. In a preferred embodiment, the bacterial component is at least one strain of Enterococci, the yeast is at least one strain of Saccharomyces, and a high lactose whey.

12 Claims, 5 Drawing Sheets

PROBIOTIC MIXTURE INTENDED FOR MONOGASTRIC ANIMALS TO CONTROL INTESTINAL FLORA POPULATIONS

BACKGROUND OF THE INVENTION

1. Field of the Invention

The invention relates to a mixture of probiotics to be fed to monogastric animals and, more specifically, a mixture of facultative anaerobic probiotic organisms affecting and controlling or inhibiting the colonization of deleterious bacteria in the intestines of monogastric animals and humans.

2. Background of the Prior Art

Probiotics are defined as microbes that are fed to animals to improve the microbial populations in the intestines of animals or humans. Most prior art probiotics are lactic acid-producing bacteria. The probiotics of the present invention include both bacteria and yeasts.

Probiotics have been fed to animals to reduce or replace the potentially pathogenic intestinal bacteria with nonpathogenic species.

Spring, March 1997; (Animal Talk), opines that the main regulatory mechanisms used by natural gut inhibitants as Lactobacilli and Enterococci is to keep pathogenic bacteria from colonizing the digestive tract. Mechanisms discussed include competition for nutrients, growth factors, intestinal receptor sites, and stimulation of epithelial cell turnover. Creation of a restrictive environment includes lower pH, VFA and lactic acid production or induction of an immunologic process or antimicrobial substances.

Presser, et al, 1997 (Appl & Environ Microbio Vol. 63 No. 6:2355–2360), observed the negative effects on the growth rate of *E. coli* as a function of pH and lactic acid concentration. The findings demonstrated *E. coli* growth rate was linearly related to the hydrogen ion concentration. In the range 0 to 100 mM lactic acid, growth rate was also linearly related to the undissociated lactic acid concentration.

Hudault et al., 1997 (Appl & Environ Microbio Vol. 63 No. 6:513–518) demonstrated an antagonistic activity exerted in vitro and in vivo by *Lactobacillus casei* (strain GG) against *Salmonella typhimurium* C5 infection. The mechanism of this antagonist activity was reported to be dependent upon an acidic environment due to lactic acid itself or alternatively to a substance that is active at low pH.

Kimura, et al., 1997 (Applied and Environmental Microbiology Vol.63, No. 9:3394–3398) found that human test subjects harbored a unique collection of Bifidobacteria and Lactobacilli species. Their results emphasized the complexity of the relationship between the intestinal microflora and the host where it appears that the host's predominant strains do not illicit as large of a IgG titer response as do nondominant intestinal species.

Perdigon, et al., 1991 (J Dairy Research Vol. 58:485–496) showed an immunoadjuvant activity of oral *Lactobacillus casei* by playing an important role in the prevention of enteric infections by increasing IgA secretion into the intestinal lumen thus providing a defense for the mucosal surface against enteric (i.e., Salmonella and *E. coli*) challenges.

Bernet, et al., 1994 (Gut 35:483–489) demonstrated *Lactobacillus acidoiphilis* LA1 binds to cultured human intestinal cell walls and inhibits cell attachment and cell invasion by enterovirulent bacteria.

Fujiwara, et al., 1997 (Appl & Environ Microbio Vol. 63 No. 6:506–512) showed that the binding inhibitor produced by *B. longum* and other Bifidobacterium species was estimated to contribute to their normal anti-infectious activities by preventing the binding of pathogenic strains of *E. coli* to their common bacterium intestinal binding structures.

Firon, et al., 1983 (Carbohydrate Res. 120:235–249) commented on carbohydrate specificity of the surface lectins of Escherichia, Kleibsiella, and Salmonella organisms.

Adlerberth, et al., 1996 (Appl & Environ Microbio Vol. 63 No. 6:2244–2251) found mannose-specific adhesions in a variety of gram-negative bacteria including members of the family Enterobacteriaceae such as Escherichia, Shigella, Enterobacter, Kleibsiella, and Salmonella and in Pseudomonas and Vibrio.

Adlerberth, et al., also found that Saccharomyces species of yeast contain mannose- containing polysaccharides in their cell walls which *E. coli* and other intestinal bacteria adhere to in a mannose-specific manner.

Jonvel, 1993 (Feed Mix Vol. 1, No. 4) citing Gedek, stated there are three possible explanations of Saccharomyces yeasts' mode of action: 1) fixation of *E. coli* on the yeast cell wall surface if *E. coli* has fimbria (i.e., the fimbria have an affinity to mannose); 2) fixation of enterotoxin on the yeast cell wall surface and are destroyed; and 3) *E. coli* destruction by lethal yeast toxin.

Abe, et al. (1995. J Dairy Science 78:2838–2846) showed that probiotics fed to newborn calves and piglets decreased frequency of diarrhea, and stimulated body weight gains and feed conversion in those animals over control animals.

Saavedra, et al., 1994 (Lancet 334:1046–1049) showed that feeding of a Bifidobacteria and Enterococci species to hospitalized human infants for prevention of diarrhea and the shedding of rotavirus.

Ozawa, et al. 1983 (Applied and Environmental Microbiology 45: 151) reported that the administration of an Enterococcus species to calves and piglets promoted colonization of beneficial bacteria and decreased the occurrence of detrimental bacteria, such as Salmonella, in the intestine.

Surawicz, et al., 1989 (Gastroenterology Vol. 96, No. 4: 961–968) showed that *Saccharomyces boulardii* significantly reduced the incidence of antibiotic-associated diarrhea in hospitalized patients. S. boulardii has antagonistic activity against a variety of bacterial pathogens. In rats and humans it increases the disaccharidase activity in intestinal mucosa which, in turn, may improve carbohydrate absorption within the host.

From the Bergey's Manual of Systematic Bacteriology 1984. it is observed that within the genera Campylobacter, Pseudomonas and most Vibrio and Clostridia species do not utilize lactose as a carbon source for growth. Also, Enterobacteriaceae, in general, are poor or nonutilizers of lactose. Whereas, the Enterococcus species used in the invention readily utilize lactose.

The importance of mannose-sensitive adhesions of gram-negative intestinal bacteria for intestinal colonization of these bacteria was investigated, as well as the presence of a mannose-specific adhesion in a gram-positive bacterial species, i.e., Lactobacilli and Enterococci, which belong to the indigenous intestinal microflora. Further, investigation was made into the ability of gram-positive, non-pathogenic Enterococci and Lactobacilli to associate with animals' intestines and mannose containing polysaccharides (mannose) found as a major cell wall component in species of Saccharomyces, and, in particular, its use in conjunction with the lactic acid-producing metabolism of Enterococci and/or Lactobacilli to rid and/or prophylatically protect the intestines of monogastric animals and humans of potentially pathogenic bacteria.

SUMMARY OF THE INVENTION

The invention consists of a defined combination of facultative anaerobic probiotic organisms effective in controlling or inhibiting the colonization of certain deleterious bacteria in the intestines of monogastric animals and humans. In a preferred embodiment of the invention, nutrients are added to the mixture of probiotics to enhance efficacy in some situations.

The invention is a unique probiotic mixture that combines two viable lactic acid-producing Enterococcus strains and two viable Saccharomyces yeast strains that are preferably added to an active carrier that includes nutrients to assist in the growth and/or activity of the probiotics. The mixture is fed to monogastric animals to control the microflora population of the intestinal tract and to maintain a proper balance of naturally occurring beneficial microflora while competing with and helping to exclude deleterious strains of microflora such as bacterial pathogens, thus aiding the ability of the animal to maintain a normal, healthy intestinal environment and, in turn, utilize feeds better.

Ingesting this probiotic mixture by monogastric animals and humans will help the body protect itself from colonization of pathogenic microflora such as bacteria within the families Enterobacteriacae and Vibrionaceae, and the genera Campylobacter, Clostridia, Pseudomonas, or other organisms that can cause intestinal distress.

An object of the present invention is to provide a mixture of probiotics which is orally administered to monogastric animals to assist the animal in protecting itself from the colonization and reproduction of pathogenic microorganisms.

Another object of the invention is to provide a mixture of probiotics for the oral administration to humans which will treat and provide a prophylactic effect on microorganisms which cause diarrhea and other intestinal distresses.

These and other objects of the invention will be made apparent to one of skill in the art upon a review and understanding of the specification, the associated drawings, and appended claims.

DETAILED DESCRIPTION OF PREFERRED EMBODIMENTS

The present invention provides a method of delivering a mixture of probiotics to the intestines of monogastric animals in order to establish a population of microflora that will competitively exclude the adherence of deleterious bacteria to the intestinal wall. It also provides viable yeast microbes that will attract and attach these deleterious microbes to the yeast's cell surface and carry them out of the body as excrement. A food source that enhances the growth of the invention's microbes but is not an effective nutrient for the pathogenic microflora may be included to assure growth and multiplication of the probiotic organisms.

Microflora such as the Enterococci of our invention effectively colonize the animal's intestines. Pathogenic microflora such as Escherichia, Shigella, Enterobacter, Kleibsiella, Pseudomonas, Salmonella and Vibrio, attach to mannose receptor compounds in the cell walls of intestinal villi. They use mannose sugars as recognition compounds for attachment onto the mucosal cells. The aforementioned pathogenic microbes prefer a relatively low acid (neutral pH) environment while the microbes of our invention prefer a more acidic environment.

The lactic acid-producing Enterococci of our invention readily use lactose as a source of food for growth and reproduction. The aforementioned deleterious microbes do not utilize lactose as well as the microbes in our invention thus resulting in a competitive starvation for this food source. Accordingly, a source of lactose or other carbohydrate or nutrient may be advantageously included in the probiotic mixture.

Once the Enterococcus organisms of our invention inhabit the animal's intestine, they begin to metabolize, reproduce and produce lactic acid which is excreted into the surrounding environment. The lactic acid lowers the pH in the area causing the neighboring harmful enteric organisms to detach from their locations on the intestinal villi due to the acidic environment.

Subsequent to the detachment from the villi attachment sites, the enteric microbes encounter the yeast strains which, like the intestinal villi, contain mannose receptor compounds in their cell walls. The aforementioned deleterious microbes use these mannose sugars as recognition compounds for attachment onto the intestinal villi. Even if the pathogenic bacteria prefer the receptor sites on the intestine over those of the yeast, the production of a poor environment for these microflora by the Enterococci via acid produced leads to the detachment of the pathogenic bacteria and their subsequent adherence to the yeast strains is observed.

The invention's yeasts do not adhere to intestinal walls and therefore, maintain themselves in the intestinal lumen where they pass through and are excreted in the manure. This passage carries any attached enteric microflora from the body.

The probiotic contains a combination of viable lactic acid-producing bacteria (including the genera Enterococcus and Lactobacillus) and a viable yeast (of the Saccharomyces genera, which have mannose-containing polysaccharides and glucans associated with their cell walls). A carbohydrate source (including whey, milk products, and lactose) which is poorly utilized by many pathogenically significant species of the families Enterobacteriaceae and Vibrionaceae; and the genera Pseudomonas, Campylobacter, and Clostridia may be advantageously included with the bacteria and yeast. The lactic acid-producing bacteria and yeast strains of the probiotic mixture grow best under mesophillic temperatures (25° C. to 40° C.) and slightly acidic conditions (pH 6.8 to 5.0), even though growth can be observed within the range of pH=4.0 to 8.0 with the lactic acid-producing bacteria and within the range of pH=3.5 to 8.0 with the yeasts.

The probiotic mixture contains between about 20% and about 80% of the Saccharomyces yeast CFUs and between about 20% and about 80% of the Enterococci bacteria CFUs, and preferably between about 30% and about 50% of the Saccharomyces yeast CFUs and between about 50% and about 70% of the Enterococci bacteria CFUs, with the preferred embodiment comprising 40% Saccharomyces and 60% Enterococci. In particular, the commercial products of the probiotic mixture of the present invention contained approximately equal quantities of the two Enterococcus strains, *Enterococcus faecium* NCIB Accession No. 11181 (commercially available from Medipharm, USA, 10215 Dennis Drive, Des Moines, Iowa, 50322), and *Enterococcus faecium* strain WN commercially available from Loders Croklaan, Inc., 24708 W. Durkee Rd., Channahon, Ill. 60410 and approximately equal quantities of the two Saccharomyces strains, *Saccharomyces cerevisiae* strains identified with the European Registry accession numbers Sc 47 (commercially available from SAF Agri, 400 S. Fourth St. # 310, Minneapolis, Minn. 55415 ) and I-1079 (commercially available from Lallemand Biochem International, 6120 West Douglas Ave. Milwaukee, Wis. 53218 ). The commercial products incorporating the probiotic mixture of the present invention are administered to provide at least $10^9$ CFUs of the Saccharomyces yeast and lactic acid-producing Enterococci combination is ingested per head per day and no adverse effects have been observed at administration rates up to $4 \times 10^9$ per head per day. Below about $2.5 \times 10^8$ CFUs per animal per day the results become variable and full efficacy may not be observed. The lactose source used in the commercial products is high-lactose whey that is available from a variety of commercial sources. In the experiments set out in this specification, the specific high-lactose whey was specified to contain between 80.0% and 88.0% lactose, between 3.0% and 5.0% crude protein, a maximum of 8.5% ash and a maximum of 5% moisture. A commercial product is constituted with the strains of Saccharomyces and Enterococci as set out above added to 1 lb. of the high-lactose whey in amounts so that there is a total of $150 \times 10^9$ CFUs of the yeast and bacteria in 1 lb. of the commercial product.

EXPERIMENT 1

The effect of the probiotic mixture on the shedding of enteric bacteria by pigs from 50 lbs. to market weight was the subject of a trial. Nine-hundred, fifty (950) 50 lb. pigs were fed a control ration consisting of a commercially accepted swine ration. Nine-hundred, fifty (950) 50 lb. pigs were fed the control ration supplemented with 2 lbs. per ton of the mixture of probiotics identified above. Manure was randomly collected from 5 animals from each group, composited, and analyzed to determine the amount of enteric bacteria shed and the feed utilization of the animals.

TABLE 1

Analyzed values of the manure (dry matter basis) of 50 lb. to 250 lb. pigs comparing control diet and diet including mixture of probiotics

| Analysis | Day 1 50 lb. pig Control Feces | Day 1 50 lb. pig Probiotic Feces | Day 100 "250 lb. pig" Feed | Day 100 "250 lb. pig" Control Feces | Day 100 "250 lb. pig" Probiotic Feces |
|---|---|---|---|---|---|
| % Starch | | | 62.79 | 5.01 | 3.68 |
| % Calcium | | | 0.54 | 1.95 | 1.10 |
| % Phosphorus | | | 0.37 | 2.64 | 2.25 |
| % Magnesium | | | 0.12 | 1.13 | 1.10 |
| pH | 6.6 | 6.6 | 6.0 | 6.4 | 6.0 |
| Enteric CFU/g | 177,000 | 2,720,000 | 0 | 1,740,000 | 125,000 |

Figure 2:
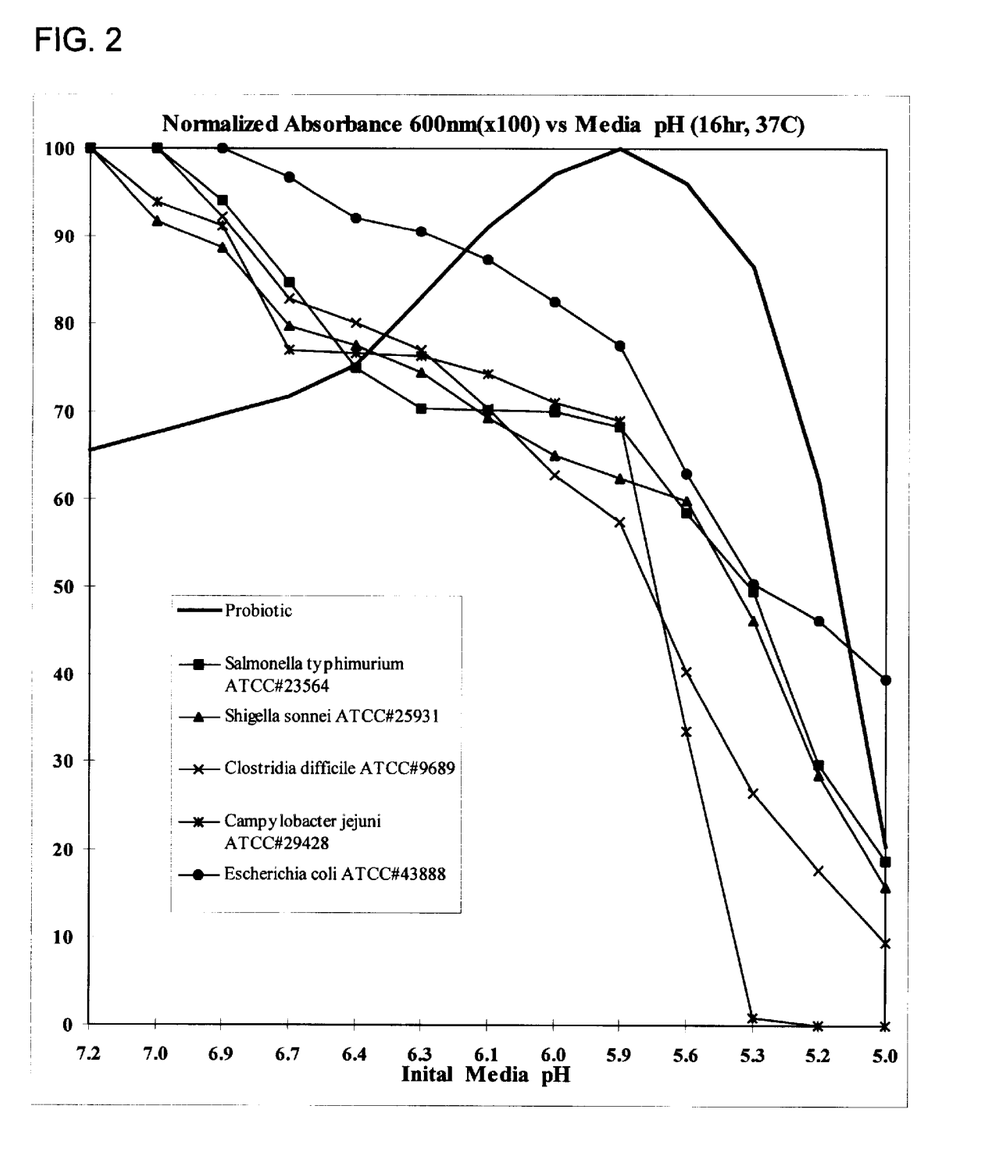
FIG. 2 is a graphical representation of the percent growth of enteric gut pathogens over a pH range and comparing the growth rate of the mixture of probiotics of the present invention.

There is observed in the data of Table 1 a marked increase in the number of enteric bacteria shed in the first day following administration of the probiotic mixture of the present invention into the ration of the test animals. There is also a marked decrease in the number of enteric bacteria shed after 100 days of treatment. Further, enhanced feed utilization is seen in the reduced amount of starch and minerals that remain in the feces of the animals being fed the mixture of probiotics of the present invention. The fecal pH of the test animals is also reduced, resulting in an environment which prefers growth of the probiotics while relatively inhibiting the growth of the enteric bacteria (see FIG. 2). The culture media used in the tests of FIG. 2 is set out in Table 2.

TABLE 2

Culture Media Substrate
(pH adjusted from 7.2 through 5.0 with 12N hydrochloric acid)

| Media (Ingredient) | Per liter (grams) |
|---|---|
| Bacto-Soytone (Difco) | 15.0 |
| Dextrose | 6.0 |
| Maltose | 6.0 |
| Sodium Chloride | 5.0 |
| Dipotassium phosphate | 5.0 |
| Monopotassium phosphate | 1.0 |
| Monosodium phosphate | 3.0 |
| De-ionized water | 1,000.0 |

EXPERIMENT 2

A similar trial was conducted on 20 sows that were fed a commercially acceptable swine ration as a control ration. The treated group of 9 sows were fed the control ration supplemented with 2 lbs. per ton of the probiotic mixture identified above.

TABLE 3

Analyzed values of the manure (dry matter basis) of sows comparing control diet and diet including mixture of probiotics for three weeks prior to sampling

| Analysis | Farrowing Feed | Farrowing Control Feces | Farrowing Probiotic Feces |
|---|---|---|---|
| % Moisture | 0.0 | 0.00 | 0.00 |
| % Dry Matter | 100.00 | 100.00 | 100.00 |
| % Crude Protein | 21.23 | 20.12 | 19.19 |
| % Starch | 45.71 | 2.28 | 1.75 |

TABLE 3-continued

Analyzed values of the manure (dry matter basis) of sows comparing control diet and diet including mixture of probiotics for three weeks prior to sampling

| Analysis | Farrowing Feed | Farrowing Control Feces | Farrowing Probiotic Feces |
|---|---|---|---|
| % Calcium | 1.52 | 6.93 | 5.91 |
| % Phosphorus | 1.12 | 4.71 | 4.19 |
| % Magnesium | 0.22 | 1.12 | 1.05 |
| pH | 6.3 | 7.3 | 6.8 |
| Enteric CFU/g | N/A | 84,200,000 | 6,910,000 |

The data in Table 3 show again the marked decrease in the amount of enteric bacteria shed in the manure of animals following three-weeks of treatment with the mixture of probiotics. Less starch, protein, and minerals are in the feces of the treated animals, demonstrating enhanced feed utilization. Also, the pH of the sows fed the mixture of probiotics is lowered, resulting in an environment which prefers growth of the probiotics while relatively inhibiting the growth of the enteric bacteria (see FIG. 2).

EXPERIMENT 3

Figure 1:
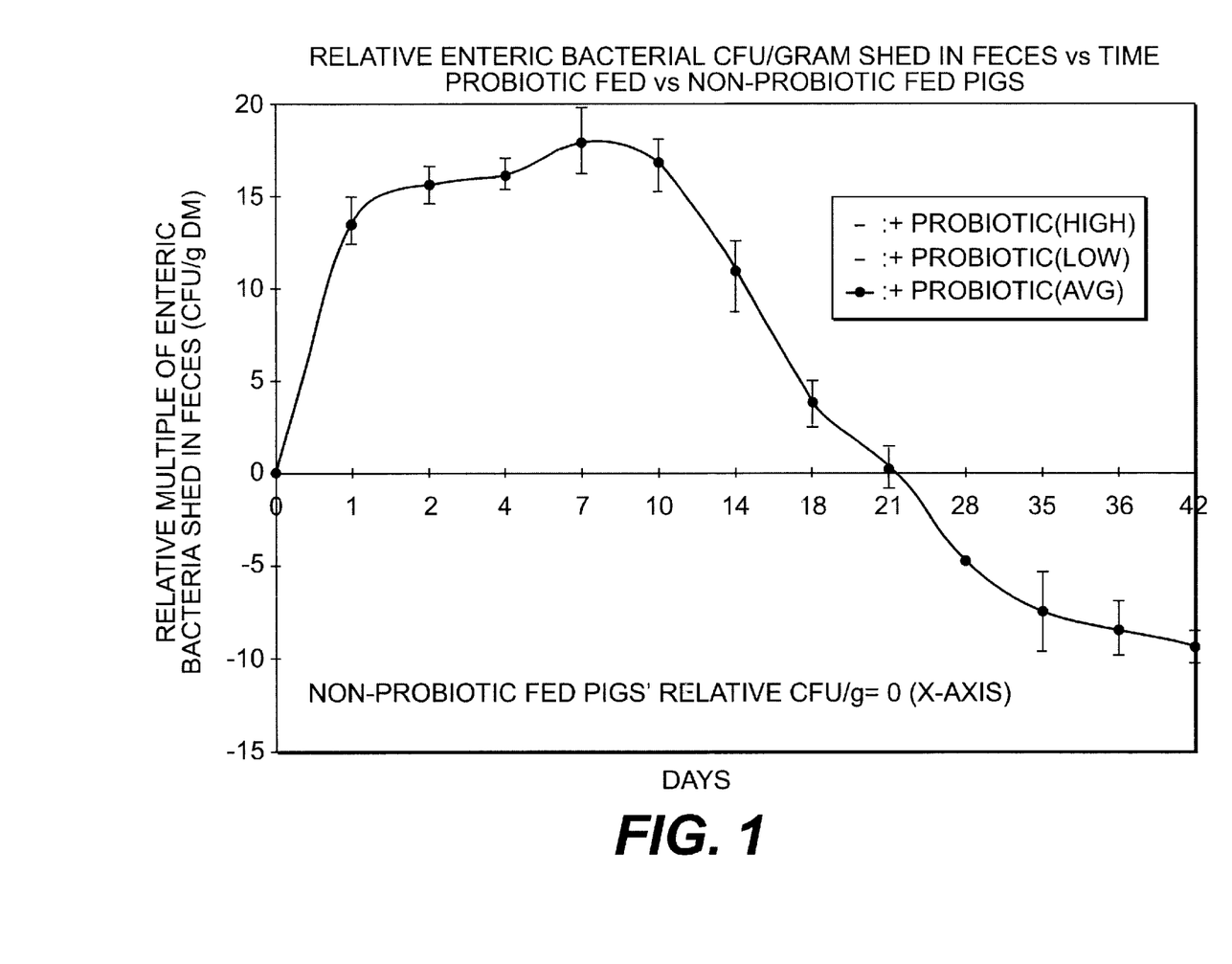
FIG. 1 is a graphical representation of the relative shed of enteric bacteria over time by swine following administration of a probiotic mixture of the present invention.

As indicated in Tables 1 and 3, there is an initial increase in the amounts of enteric bacteria shed by animals that have been administered the mixture of probiotics of the present invention, followed sometime later by a reduction in the amount of such bacteria being shed by the treated animals relative to control animals. The amount of enteric bacteria shed over time was measured and the results are presented in FIG. 1. The data in FIG. 1 were compiled from swine trials comparing pigs fed a control diet with pigs fed the control diet supplemented with the mixture of probiotics of the present invention. The enteric bacteria shed by the control pigs is represented in the figure by the baseline at 0. The data show that there is an initial, almost immediate increase in enteric bacterial shedding which peaks at about 6 to 8 days, followed by a generally linear decrease to about 28 days and a continuing, though less steep, decrease thereafter. The probiotic mixture is observed to cause an immediate shedding of the existing contamination of enteric bacteria from the gut of the treated animals followed by a very marked decline in the population of the enteric bacteria in the treated animal down to approximately nine times lower than the level of enteric bacterial contamination of the control animals.

EXPERIMENT 4

The lactic acid-producing bacteria included in the mixture of probiotics prefer a lower pH environment than do the enteric bacteria. This is shown in the data presented in FIG. 2. Using a culture substrate of soy protein and glucose as set out in Table 4, the growth rate of various gut pathogens over a range of pH was measured and compared to the growth rate of the mixture of probiotics.

TABLE 4

Culture Media Substrate
pH adjusted from 7.00 through 4.88 with 12N hydrochloric acid)

| Media (Ingredient) | Per liter (grams) |
|---|---|
| Bacto-Soytone (Difco) | 15.0 |
| Dextrose | 6.0 |
| Sodium Chloride | 5.0 |
| Dipotassium phosphate | 5.0 |
| Monopotassium phosphate | 1.0 |
| Monosodium phosphate | 3.0 |
| De-ionized water | 1,000.0 |

Figure 5:
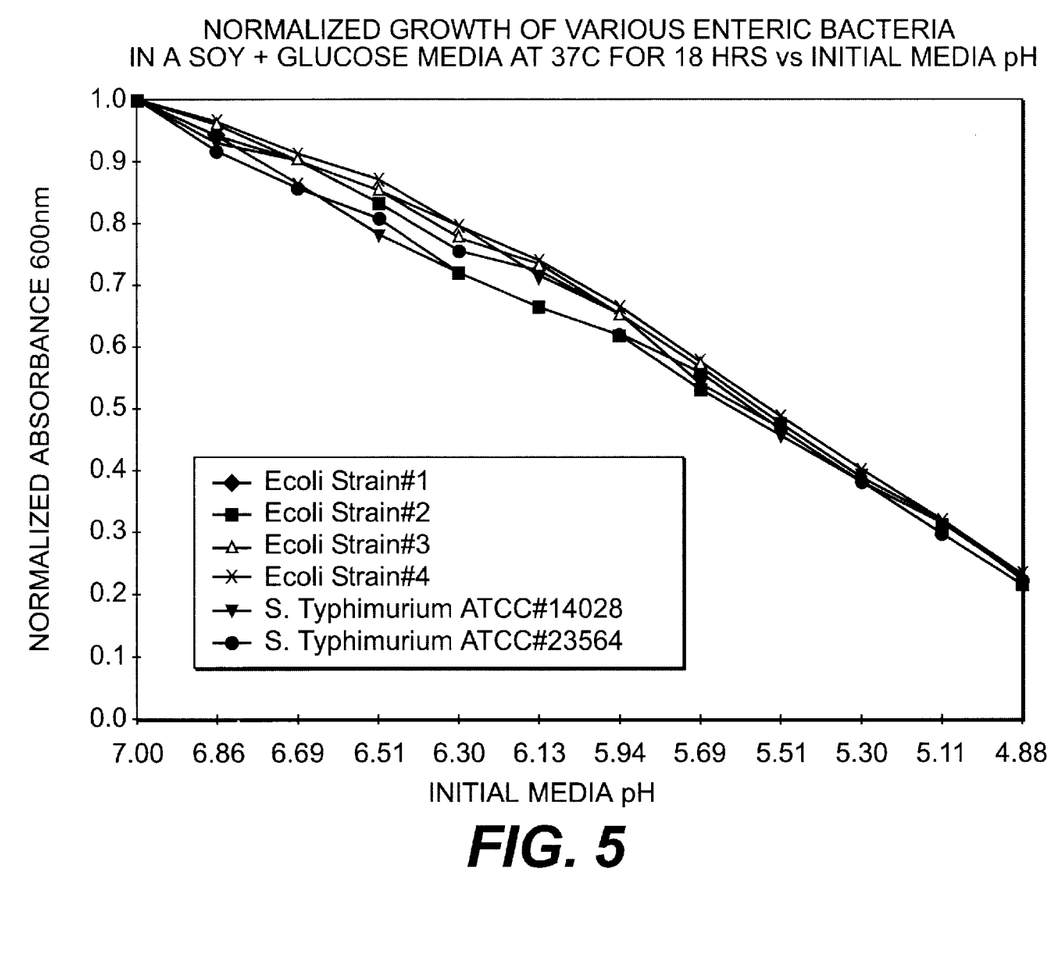
FIG. 5 is a graphical representation of data showing the decline in growth rate with pH of four strains of $E.$ $coli$ and two strains of Salmonella enteric bacteria.

As can be seen in FIG. 2, the enteric bacteria have a growth rate which declines as the pH falls from neutral (7.2) to a pH of 5, whereas the probiotic growth rate increased until a pH of about 5.8. A similar test was conducted using the same substrate to observe the pH dependence of growth rates of four strains of *E. coli* and two accessions of strains of Salmonella (FIG. 5). Each of the *E. coli* and Salmonella strains, when normalized to 100% at a pH of 7, showed a generally linear decrease in growth rates down to a pH of 5.

EXPERIMENT 5

A herd of pigs that had a history of chronic infection of Clostridia was divided into four groups to observe the effects of treatment with the probiotic mixture before and after farrowing. In the data of Table 5, Group 1 is the control; Group 2 were administered the probiotic mixture between days 7 and 14 following farrowing; and Groups 3 and 4 were administered the probiotic mixture for three weeks before farrowing.

TABLE 5

Data on effects of probiotic mixture on farrowing gilts with chronic Clostridia infections

| | No. Litters | Total Pigs | No. Pigs Treated for Clostridia | No. of Clostridia deaths | No. of Pigs >8 lbs. | No. of Pigs <8 lbs. | No. of Pigs "No value" | Avg. Pig wt at 14 days (lbs.) |
|---|---|---|---|---|---|---|---|---|
| Group 1 | 18 | 160 | 108 | 7 | 146 | 4 | 3 | 10.8 |
| Group 2 | 19 | 158 | 60 | 2 | 154 | 2 | 0 | 12.0 |
| Group 3 | 27 | 216 | 0 | 0 | 216 | 0 | 0 | 11.8 |
| Group 4 | 22 | 120 | 0 | 0 | 118 | 0 | 2 | 12.0 |

TABLE 6

Data on effects of probiotic on pigs born to farrowing gilts with chronic Clostridia infections

|  | % Pigs Treated for Clostridia | % Pigs > 8 lbs. |
|---|---|---|
| Group 1 | 67.5 | 91.3 |
| Group 2 | 38.0 | 97.5 |
| Group 3 | 0.0 | 100.0 |
| Group 4 | 0.0 | 98.3 |

Figure 3:
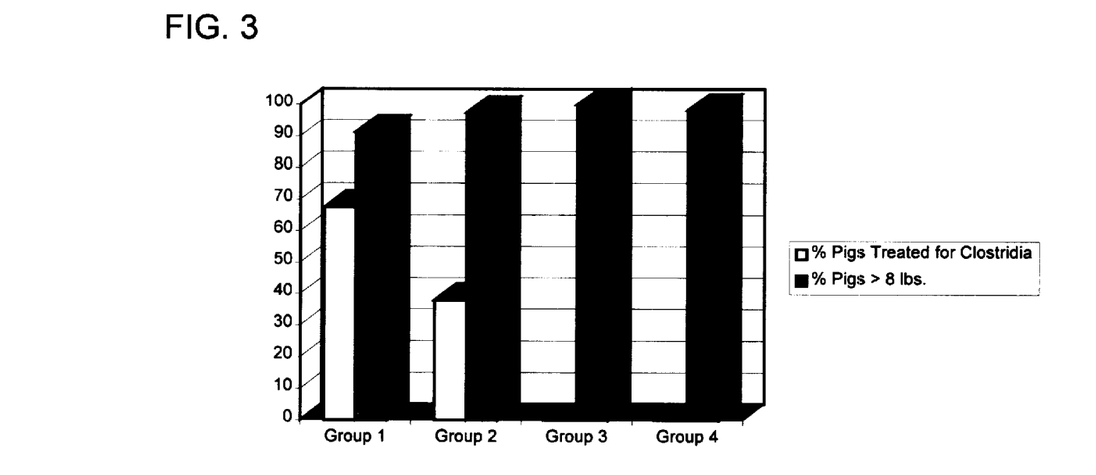
FIGS. 3 and 4 are a graphical representation of data regarding piglets from gilts with chronic Clostridia treated with the probiotic mixture of the present invention.
Figure 4:
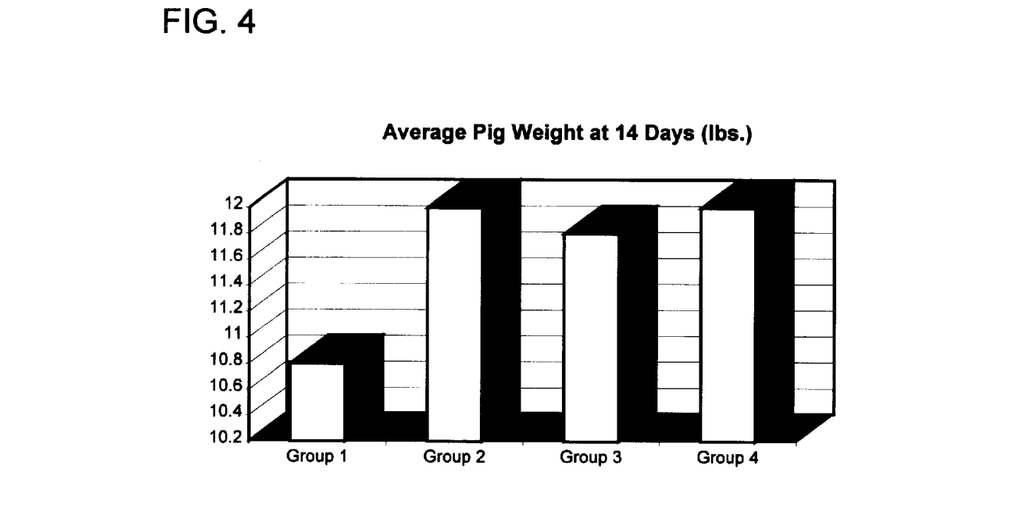

The data show the average litter weights of gilts fed the probiotic mixture was one pound heavier at 14 days compared to the pigs of gilts fed the control diet, and a greater percentage of the piglets born to gilts on the probiotic-treated diet were heavier at 8 lbs. at 14 days. Also, the number of piglets that required treatment for Clostridia infections of the treated gilts was lower than piglets of the control gilts. A graphical representation of this summary data is shown in FIGS. 3 and 4.

EXPERIMENT 6

The mixture of probiotics was incubated inside six-inch segments of porcine small intestine to monitor the detachment of enteric bacteria from the intestine tissue over time. A detailed treatment of the trials is shown in Table 7A, and a summary of the results of the trials is presented in Table 7B.

A first trial looked at the effect of the addition of the probiotic upon the indigenous enteric microflora of the small intestine of two different 10 lb. piglets. Two 6-inch ligations of freshly slaughtered small intestine were rinsed three times with 10 mL sterile, phosphate buffered saline (PBS) pH=7.2. The third 10 mL rinse was saved and analyzed for enteric bacteria (using Hektoen-Enteric Agar, BBL). These values are the Time initial (Ti, Pre-addition of Probiotic). A fourth aliquot of PBS (10 mL), $6\times10^7$ CFU of the probiotic mixture was added to the 6-inch sections of small intestine. The inoculated intestines were tied-off with sterile surgical string, and incubated at 37° C. for 4 hours in a gently shaking water bath (rpm=65). After 4 hours, the intestinal fluids were collected, rinsed three times with 10 ML PBS and analyzed for enteric bacteria via Hektoen-Enteric Agar (BBL). The results indicated a significant number of enteric bacteria were liberated from the probiotic-treated intestinal sections.

To substantiate the results of the first trial, a second trial with controls was conducted using four 6-inch sections of the illium of the small intestine from a freshly slaughtered 220 lb. hog. Trial 2 looked at the effect of the addition of the probiotic upon the indigenous enteric microflora of the porcine small intestine. A thirty-six inch ligation of porcine small intestine was collected and cut into 6-inch sections. The treatments to the intestine were applied to non-adjacent sections from the original 36-inch ligation (i.e., section 1-control; section 2-probiotic; section 3-control; section 4-probiotic). As in Trial 1, the small intestines were rinsed three times with 10 mL PBS. In the first and third sections, 10 mL of sterile PBS was added; in the second and fourth sections, a 10 mL aliquot of PBS to which had been added $5\times10^4$ CFUs of the probiotic mixture was added. The intestine sections were subsequently tied-off and incubated at 37° C. for 4 hours in a gently shaking water bath (65 rpm). After 4 hours, the intestinal fluids were collected, rinsed three times with 10 mL PBS and analyzed for enteric bacteria via Hektoen-Enteric Agar (BBL). These analyzed values would quantitate the "free" (non-intestinally attached) enteric bacteria. The results of Trial 2 show 2.6 times more enteric bacteria were liberated (on average) from the probiotic-treated sections than the control sections.

TABLE 7A

Total CFUs Added and Collected from Small Intestine Sections

|  | Enterics | Yeasts | Enterococci | Total CFU Added |
|---|---|---|---|---|
| Time = 0 Total CFUs Added to 6-inch Section of Small Intestine | | | | |
| Control, Rep #1 | 0 | 0 | 0 | 0 |
| Control, Rep #2 | 0 | 0 | 0 | 0 |
| Probiotic, Rep #1 | 0 | $2.33 \times 10^3$ | $4.8 \times 10^4$ | $5.03 \times 10^4$ |
| Probiotic, Rep #2 | 0 | $2.25 \times 10^3$ | $5.10 \times 10^4$ | $5.33 \times 10^4$ |
| Time = 4 Total CFUs Collected from 6-inch Section of Small Intestine | | | | |
| Control, Rep #1 | $3.40 \times 10^5$ | 0 | $2.83 \times 10^7$ | $2.86 \times 10^7$ |
| Control, Rep #2 | $4.40 \times 10^5$ | 0 | $2.14 \times 10^7$ | $2.18 \times 10^7$ |
| Probiotic, Rep #1 | $8.50 \times 10^5$ | $2.93 \times 10^3$ | $7.41 \times 10^7$ | $7.50 \times 10^7$ |
| Probiotic, Rep #2 | $1.20 \times 10^6$ | $2.14 \times 10^3$ | $8.56 \times 10^7$ | $8.68 \times 10^7$ |

TABLE 7B

Liberated "free" enteric bacteria from porcine intestinal tissue following addition of probiotic mixture

|  | Total Enteric CFUs Detached | Relative Amount |
|---|---|---|
| Trial 1 | | |
| Rep 1 | | |
| Pre-addition of probiotic (Ti) | 10,000 | |
| 4 hrs. post-addition | 640,000 | +64X |
| Rep 2 | | |
| Pre-addition of probiotic (Ti) | 8,000 | |
| 4 hrs. post-addition | 204,000 | +25X |
| Trial 2 | | |
| Rep 1 | | |
| 4 hrs. (untreated) | 340,000 | |
| 4 hrs. post-addition | 850,000 | +2.5X |
| Rep 2 | | |
| 4 hrs. (untreated) | 440,000 | |
| 4 hrs. post-addition | 1,200,000 | +2.7X |

EXPERIMENT 7

An experiment was conducted to quantitate the production of lactic acid by the two strains of Enterococci used in the probiotic mixture of the preferred embodiment of the invention. The bacteria were grown on a soy protein/sugar substrate wherein the three sugars lactose, glucose and maltose were used. The substrates were made up as shown in Table 8.

TABLE 8

Culture Media Substrate (pH = 6.9 +/- 0.1 units)

| Media (Ingredient) | Per liter (grams) |
|---|---|
| Bacto-Soytone (Difco) | 15.0 |
| Carbohydrate source | 10.0 |

TABLE 8-continued

| Culture Media Substrate (pH = 6.9 +/− 0.1 units) | |
|---|---|
| Media (Ingredient) | Per liter (grams) |
| Sodium Chloride | 3.6 |
| De-ionized water | 1,000.0 |

Figure 6:
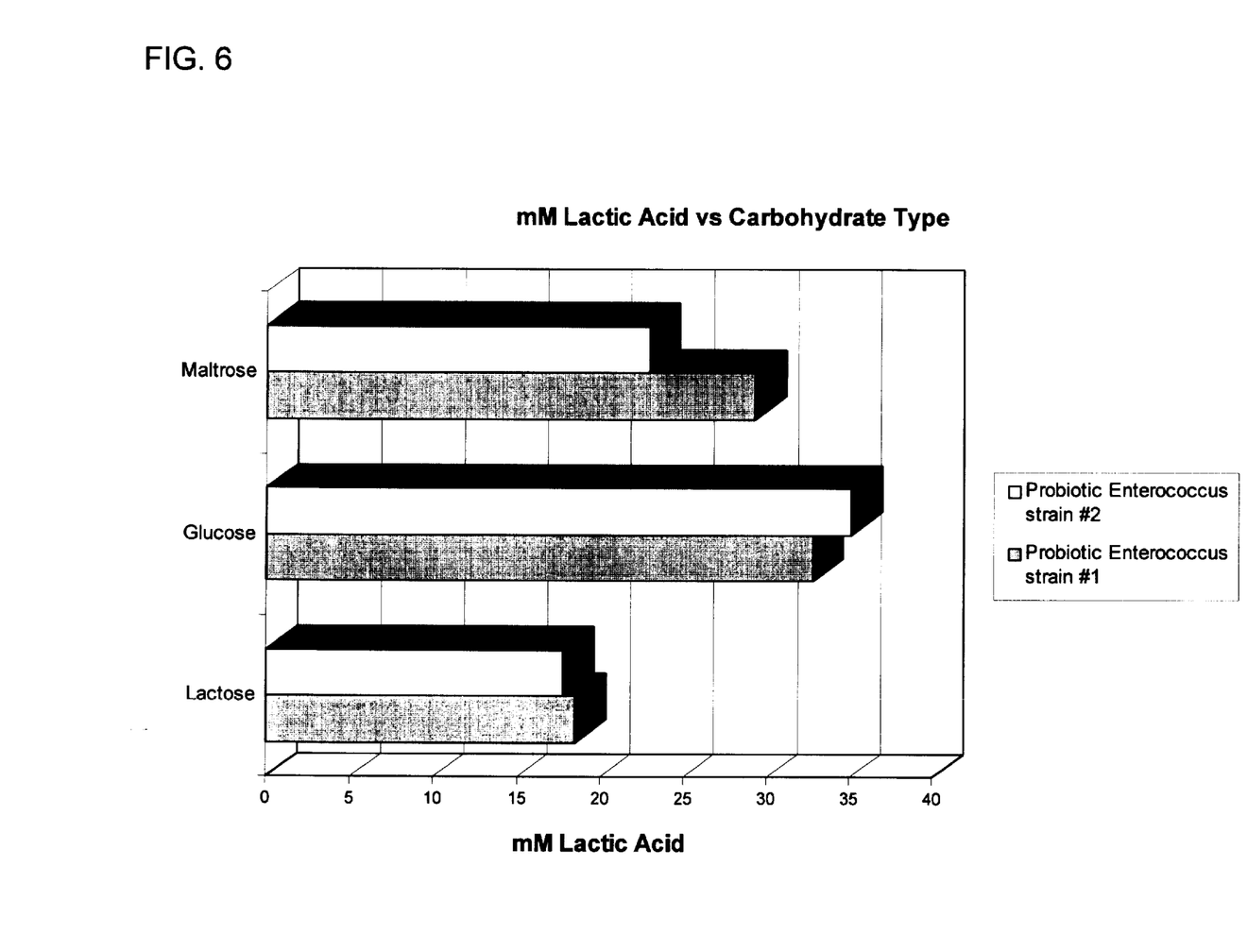
FIG. 6 is a graphical representation of the production of lactic acid by the two different Enterococci bacteria strains used in the preferred embodiment of the present invention in the presence of lactose, glucose, and maltose.

Five mL of the media was inoculated with $10^5$ CFUs of the bacteria. The substrates were incubated at 37° C. for 21 hrs and the concentration of lactic acid was measured. The lactic acid was analyzed by capillary electrophoresis (Beckman 5510 series), using 10 mM benzoic acid and 0.5 mM CTAB (hexadecyltrimethylammonium bromide) buffer (pH=4.94), kV=15, open capillary. The results are illustrated in FIG. 6.

EXPERIMENT 8

An experiment was conducted to observe the use of lactose as a carbohydrate source for lactic acid production and growth of the probiotic strains of Enterococcus and its utilization or non-utilization by the other microbes tested. The microbes were grown on the media set out in Table 9.

TABLE 9

| Culture Media Substrate (pH = 6.9 +/− 0.1 units) | |
|---|---|
| Media (Ingredient) | Per liter (grams) |
| Bacto-Soytone (Difco) | 15.0 |
| Lactose | 10.0 |
| Sodium Chloride | 3.6 |
| De-ionized water | 1,000.0 |

In the experiment, 5 mL of the media was inoculated with $10^4$ CFUs of the respective strain of microbe. The substrates were incubated at 37° C. for 18 hrs and the concentration of lactic acid was measured. The lactic acid was analyzed by capillary electrophoresis (Beckman 5510 series), using 10 mM benzoic acid and 0.5 mM CTAB (hexadecyltrimethylammonium bromide) buffer (pH=4.94), kV=15, open capillary. The results are illustrated in Table 10.

TABLE 10

Lactic Acid Production of Strains of Various Microbes

| ATCC # | Microbial ID | MM lactic acid (18 hrs at 37° C.) |
|---|---|---|
|  | Probiotic Enterococcus strain #1 | 13.3 |
|  | Probiotic Enterococcus strain #2 | 15.6 |
| 25931 | *Shigella sonnei* | 2.1 |
| 11835 | *Shigella dyseneriae* | $0^1$ |
| 23564 | *Salmonella typhimurium* | $0^1$ |
| 14028 | *Salmonella typhimurium* | $0^1$ |
| 43888 | *Escherichia coli* 0157:H7 | 4.4 |
| 10145 | *Pseudomonas aeruguinosa* | $0^1$ |
| 29428 | *Campylobacter jejuni* | $0^1$ |
| 9689 | *Clostridia difficile* | $0^1$ |
| 14034 | *Vibrio cholerae* | $0^1$ |

[1]Detection limit is 0.1 mM, values less than 0.1 mM are given as 0.

EXPERIMENT 9

An experiment was conducted to observe the adherence of various bacterial strains to the Saccharomyces yeast strains used in the probiotic mixture of the present invention. The bacterial strains tested are listed in Table 11.

TABLE 11

Bacterial Strains

| ATCC # | Microbe Tested |
|---|---|
| 25931 | *Shigella sonnei* |
| 23564 | *Salmonella typhimurium* |
| 14028 | *Salmonella typhimurium* |
| 43888 | *Escherichia coli* 0157:H7 |
| 10145 | *Pseudomonas aeruguinosa* |
| 29428 | *Campylobacter jejuni* |
| 9689 | *Clostridia difficile* |

The Saccharomyces yeast strains of the probiotic mixture and the bacterial strains tested were grown on appropriate media, as listed below and in the following Tables 12 and 13.

TABLE 12

| Culture Media Substrate for Saccharomyces Yeast Strains (pH = 6.9 +/− 0.1 units) | |
|---|---|
| Media (Ingredient) | Per liter (grams) |
| Trypticase soy broth | 8.0 |
| Dextrose | 8.0 |
| Sucrose | 8.0 |
| Malt Extract | 8.0 |
| De-ionized water | 1,000.0 |

TABLE 13

| Culture Media Substrate for Salmonella, Escherichia, Shigella and Kleibsiella species (pH = 7.0 +/− 0.2 units) | |
|---|---|
| Media (Ingredient) | Per liter (grams) |
| Pancreatic digest of casein | 10.0 |
| Dextrose | 3.0 |
| Sodium chloride | 5.0 |
| Yeast extract | 5.0 |
| Calcium chloride | 1.0 |
| De-ionized water | 1,000.0 |

For other species, commercial media were used: Clostridium species—Reinforced Clostridial Medium (Difco); Campylobacter species—Fluid Thioglycollate Medium (Difco); Pseudomonas species—Trypticase Soy Broth (BBL).

All cultures were grown for 18 hrs at 37° C. in the appropriate medium. The organisms were centrifuged at 7,000 rpm for 30 minutes and washed twice with PBS (pH=7.2). After the second wash, the cells were resuspended in PBS to produce a McFarland #2 standard of turbidity. Next, 0.2 mL of the appropriate bacterial resuspension and 0.1 mL of the Saccharomyces resuspension were co-incubated for 5 mins at 37° C. in a shaking water bath (rpm=65). After shaking, the mixtures were held at 4° C. for 4 hrs. The mixed cultures were Gram-stained and a sample deposited on a microscope slide. The stained slides were observed under 1,500 magnification to determine the interaction between the bacterial strains being tested and the Saccharomyces. Adherence of the bacteria to the Saccharomyces strains was observed for all bacterial species.

EXPERIMENT 10

An experiment was conducted to observe the lactic acid and acetic acid production over time of a strain of *E. coli*, the Enterococci species of the probiotic mixture, the Saccharomyces species of the probiotic mixture alone and in combination with the E. coli strain. In the experiment, $10^7$ CFUs of each microbe were added to 250 mL of the media culture set out in Table 14.

TABLE 14

| Culture Media Substrate (pH = 7.0 +/− 0.1 units) | |
|---|---|
| Media (Ingredient) | Per liter (grams) |
| Bacto-Soytone (Difco) | 5.0 |
| Dextrose | 1.0 |
| Maltose | 3.5 |
| Sodium Chloride | 3.6 |
| Dipotassium phosphate | 1.0 |
| Trypticase soy broth (BBL) | 1.0 |
| Soluble starch | 0.5 |
| De-ionized water | 1,000.0 |

Ten mL aliquots were taken and analyzed prior to inoculation (at 37° C. in a gently shaking water bath at 65 rpm) and at 2, 4, 6 and 8 hrs post-inoculation. The lactic acid was analyzed by capillary electrophoresis (Beckman 5510 series), using 10 mM benzoic acid and 0.5 mM CTAB (hexadecyltrimethylammonium bromide) buffer (pH=4.94), kV=15, open capillary. The results are set out in Table 15.

TABLE 15

| Lactic Acid and Acetic Acid Production Over Time | | | | | |
|---|---|---|---|---|---|
| | mM lactic acid | | | | |
| Culture ID | 0 hr | 2 hrs | 4 hrs | 6 hrs | 8 hrs |
| E. coli ATCC #43888 (only) | $0.0^1$ | 0.3 | 0.8 | 1.4 | 2.6 |
| Probiotic Enterococci mixture (only) | $0.0^1$ | 0.8 | 4.2 | 8.1 | 13.9 |
| Probiotic Saccharomyces mixture (only) | $0.0^1$ | $0.0^1$ | $0.0^1$ | $0.0^1$ | $0.0^1$ |
| E. coli + Enterococci | $0.0^1$ | 0.7 | 4.3 | 8.4 | 14.2 |
| E. coli + Saccharomyces | $0.0^1$ | 0.3 | 0.8 | 1.4 | 2.5 |
| E. coli ATCC #43888 (only) | $0.0^1$ | 0.6 | 1.0 | 2.4 | 3.5 |
| Probiotic Enterococci mixture (only) | $0.0^1$ | $0.0^1$ | $0.0^1$ | $0.0^1$ | $0.0^1$ |
| Probiotic Saccharomyces mixture (only) | $0.0^1$ | $0.0^1$ | $0.0^1$ | $0.0^1$ | $0.0^1$ |
| E. coli + Enterococci | $0.0^1$ | 0.6 | 1.1 | 1.8 | 2.7 |
| E. coli + Saccharomyces | $0.0^1$ | 0.7 | 1.1 | 2.4 | 3.6 |

[1]Detection limit is 0.1 mM, values less than 0.1 mM are given as 0.

These results suggest that the ability of the Enterococci strains of the probiotic mixture to produce lactic acid are not hindered nor greatly influenced by the E. coli isolate. Also, ability of the E. coli isolate to metabolize appears to be hindered when co-incubated with the Enterococci as seen in the acetic acid results at 6 and 8 hrs and the marked depression of acetic acid formation relative to E. coli only and to E. coli +Saccharomyces. At 6 hrs and beyond, the lactic acid concentration was greater than 8 mM. Further, the Saccharomyces strains do not seem to hinder the ability of the E. coli isolate to metabolize and produce acids.

Although the invention has been described with respect to a preferred embodiment thereof, it is to be also understood that it is not to be so limited since changes and modifications can be made therein which are within the full intended scope of this invention as defined by the appended claims.

We claim:

1. A probiotic product comprising:

(a) one or more viable lactic acid-producing bacteria strains within the genus of Enterococcus;

(b) one or more viable yeast strains within the genus of Saccharomyces; and (c) one or more carbohydrate sources capable of being used by said one or more bacteria strains as a food source for growth, wherein said probiotic product is suitable for oral administration to humans or monogastric animals and controls enteric bacteria populations in the intestines of said humans or monogastric animals upon administration and wherein between 30% and 50% of colony forming units (CFUs) of said probiotic product are Saccharomyces yeast CFUs, and between 50% and 70% CFUs of said probiotic product are Enterococcus bacteria CFUs.

2. The probiotic product as defined in claim 1, wherein said one or more carbohydrate sources are one or more sugars selected from the group consisting of glucose, fructose, lactose, maltose, and sucrose.

3. The probiotic product according to claim 1, wherein said one or more yeast strains are selected from the group consisting of Saccharomyces cerevisiae strains Sc 47 (NCYC #47) and I-1079 (CNCM #I-1079).

4. A food supplement comprising the probiotic product of claim 1.

5. The probiotic product according to claim 1, wherein said one or more carbohydrate sources comprises whey.

6. The probiotic product according to claim 5, wherein said whey comprises between 80.0% and 88.0% lactose.

7. The probiotic product according to claim 1, wherein said one or more carbohydrate sources comprises a milk product.

8. The probiotic product according to claim 1, wherein said one or more carbohydrate sources comprises lactose.

9. The probiotic product according to claim 8, comprising two Saccharomyces yeast strains and two Enterococcus bacteria strains.

10. The probiotic product according to claim 1, wherein said one or more carbohydrate sources comprises fructose.

11. The probiotic product according to claim 10, comprising two Saccharomyces yeast strains and two Enterococcus bacteria strains.

12. The probiotic product according to claim 1, comprising Enterococcus faecium strain 11181 (NCIMB #11181).

* * * * *